US011512075B2

(12) United States Patent
Shenvi et al.

(10) Patent No.: US 11,512,075 B2
(45) Date of Patent: Nov. 29, 2022

(54) SYNTHESIS OF 20-NOR-SALVINORIN A

(71) Applicant: THE SCRIPPS RESEARCH INSTITUTE, La Jolla, CA (US)

(72) Inventors: Ryan Shenvi, San Diego, CA (US); Jeremy Roach, San Diego, CA (US); Yusuke Sasano, Sendai (JP); Laura Bohn, Jupiter, FL (US); Cullen Schmid, Cambridge, MA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 16/622,111

(22) PCT Filed: Jun. 7, 2018

(86) PCT No.: PCT/US2018/036416
§ 371 (c)(1),
(2) Date: Dec. 12, 2019

(87) PCT Pub. No.: WO2018/231618
PCT Pub. Date: Dec. 20, 2018

(65) Prior Publication Data

US 2020/0131162 A1 Apr. 30, 2020

Related U.S. Application Data

(60) Provisional application No. 62/519,363, filed on Jun. 14, 2017.

(51) Int. Cl.
*C07D 407/04* (2006.01)
*A61P 17/04* (2006.01)
*C07C 69/757* (2006.01)
*C07D 307/54* (2006.01)

(52) U.S. Cl.
CPC ............ *C07D 407/04* (2013.01); *A61P 17/04* (2018.01); *C07C 69/757* (2013.01); *C07D 307/54* (2013.01)

(58) Field of Classification Search
CPC .. C07D 407/04; C07D 307/54; C07C 69/757; A61P 17/04
See application file for complete search history.

(56) References Cited

U.S. PATENT DOCUMENTS 7,728,001 B2 * 6/2010 Prisinzano ............ C07F 7/1804 514/297
8,492,564 B2 * 7/2013 Beguin ................... A61P 25/18 549/60
10,125,129 B2 * 11/2018 Prisinzano ........... C07D 407/14

FOREIGN PATENT DOCUMENTS

WO WO-2008119097 A1 * 10/2008 ........... A61K 36/537

OTHER PUBLICATIONS

Bergman; J. Org. Chem. 2009, 74, 6, 2589-2591. (Year: 2009).*
Butelman; Front. Pharmacol 2015, 6, 190. doi: 10.3389/fphar.2015.00190 (Year: 2015).*
Ivanova; Medicinal Chemistry Research 2015, 24, 2257. doi: 10.1007/s00044-013-0866-z (Year: 2015).*
Johnson; Drug and Alcohol Dependence 2011, 115, 150-155. doi:10.1016/j.drugalcdep.2010.11.005 (Year: 2011).*
Lanfranchi; Eur. J. Org. Chem. 2011, 2818-2826. DOI: 10.1002/ejoc.201100207 (Year: 2011).*
Line; Chem.Eur.J. 2016, 22, 17983-17986. DOI:10.1002/chem.201604853 (Year: 2016).*
Lovell; Topics in Current Chemistry, 2011, 299, 141-185. https://doi.org/10.1007/128_2010_82 (Year: 2011).*
MacLean; Psychopharmacology 2013, 226, 381-392. doi: 10.1007/s00213-012-2912-9 (Year: 2013).*
Roach; ACS Cent. Sci. 2017, 3, 12, 1329-1336. doi: 10.1021/acscentsci.7b00488 (Year: 2017).*
Roach; ChemRxiv 2017, 1-3. doi: 10.26434/chemrxiv.5318188.v1 (Year: 2017).*
Scheerer; J. Am. Chem. Soc. 2007, 129, 29, 8968-8969. doi: 10.1021/ja073590a (Year: 2007).*
National Center for Biotechnology Information. PubChem Compound Summary for CID 102425243, 20-Norsalvinorin A. Create Date Dec. 26, 2015. https://pubchem.ncbi.nlm.nih.gov/compound/20-Norsalvinorin-A. (Year: 2015).*
Hagiwara; J. Org. Chem. 2005, 70, 6, 2250-2255. DOI: 10.1021/jo0478499 (Year: 2005).*
Hirasawa; Bioorganic & Medicinal Chemistry Letters 2018, 28, 2770-2772. https://doi.org/10.1016/j.bmcl.2018.01.055 (Year: 2018).*
Roach; Bioorganic & Medicinal Chemistry Letters 2018, 28, 1436-1445. https://doi.org/10.1016/j.bmcl.2018.03.029 (Year: 2018).*
Sherwood; J. Med. Chem. 2017, 60, 3866-3878. http://dx.doi.org/10.1021/acs.jmedchem.7b00148 (Year: 2017).*

* cited by examiner

*Primary Examiner* — Daniel R Carcanague
(74) *Attorney, Agent, or Firm* — Jennifer Kisko; Hugh Wang; Thomas Fitting

(57) ABSTRACT

The invention provides 20-nor-salvinorin A, an analog of the kappa-opioid agonist salvinorin A. The 20-nor-salvinorin A is an active kappa-opioid modulator and can be used for treatment of medical conditions wherein modulation of the kappa-opioid receptor is medically indicated, such as pain, pruritis, depression, or inflammation, or conditions implicating perception and consciousness. 20-nor-salvinorin A can be less additive when used in treatment compared to a mu-opioid receptor agonist, and 20-nor-salvinorin A is more stable in vivo than is parent compound salvinorin A. The invention further provides synthetic intermediates and procedures for preparation of 20-nor-salvinorin A.

6 Claims, 5 Drawing Sheets

SYNTHESIS OF 20-NOR-SALVINORIN A

CROSS-REFERENCE TO RELATED APPLICATION

This application claims the priority of U.S. provisional application Ser. No. 62/519,363, filed Jun. 14, 2017, the disclosure of which is incorporated by reference herein in its entirety.

STATEMENT OF GOVERNMENT SUPPORT

This invention was made with government support under grant numbers GM104180, GM105766 and DA031927 awarded by the National Institutes of Health. The government has certain rights in the invention.

BACKGROUND

Salvinorin A (SalA) is a plant metabolite that agonizes the human kappa-opioid receptor (KOR) at high affinity. Its therapeutic potential has stimulated extensive semi-synthetic studies and total synthesis campaigns. However, structural modification of SalA has been complicated by its instability, and efficient total synthesis has been frustrated by its dense, complex architecture.

The kappa-opioid receptor (KOR) is a G protein-coupled receptor (GPCR) that is heterogeneously expressed throughout the nervous system and mediates consciousness, cognition, mood and motor control. Agonism of the KOR stimulates canonical $G\alpha_i$ signaling, as well as the recruitment of β-arrestin. So-called 'biased KOR agonists' selectively activate one signaling cascade in preference to the other and mediate different effects at the cellular, network and organism level. For example, next-generation analgesics under development agonize the peripheral KOR to produce antinociception (G protein associated) in absence of common side-effects like dysphoria (β-arrestin associated).

Among the more potent agonists of the KOR is the diterpenoid plant metabolite salvinorin A (SalA), which was identified as the primary psychoactive principle of *Salvia divinorum* and the most potent naturally-occurring hallucinogen ever reported. As a result, SalA has been subject to semi-synthetic modification and total synthesis to adjust its chemical properties and promote biased signaling of the KOR. Notably, a covalent electrophile based on SalA was shown to strongly bias towards G protein-coupled signaling. While many semi-synthetic analogs of SalA have been explored, the most prolific investigators recently noted that its "chemical liabilities . . . narrow the available pool of viable chemical transformations."

20-nor-salvinorin A has never been synthesized or tested for bioactivity. The structure is broadly claimed as part of a genus in U.S. Pat. No. 7,728,001 (Prisinzano et al.), but no synthesis is provided for the nor-20 compound, nor is any such route suggested by the patent, because all the synthetic routes shown therein start with the sequiterpene moiety of the molecule already intact, bearing the C-20 methyl group. Selective removal of 20-methyl group is not described or suggested by the '001 patent, and applicants are not aware of any method for achieving this difficult transformation.

In Y. L. Bergmann, et al., J. Org. Chem. (2009), 74, 2589-2591, a synthesis of nor-20-salvinorin is suggested, but not accomplished, for the purposes of evaluating structure-activity relationships associated with C20. The authors start with 3-furaldehyde and obtain a dehydrosalvinorin intermediate lacking the 2-acetoxy group, the 4-methoxy-carbonyl group, and with undefined C-8 stereochemistry. The note states that a complete paper would appear once the synthesis was completed, but to the best of Applicants' knowledge, no such paper has ever been published. The present synthesis takes an entirely different synthetic approach and for an entirely different reason: removal of C20 dramatically simplifies synthesis and stabilizes the salvinorin scaffold. The Applicants seek to alter chemical properties at other positions on the scaffold, not probe the functional affects of C20. Furthermore, the key aromatic (furyl or other) group is added to the sesquiterpene skeleton late in the synthesis.

SUMMARY 20-nor-salvinorin A (20-nor-SalA, 20-nor-1), analogous to the natural product salvinorin A, (SalA, 1) but lacking the 20-methyl group, possesses the chemical structure

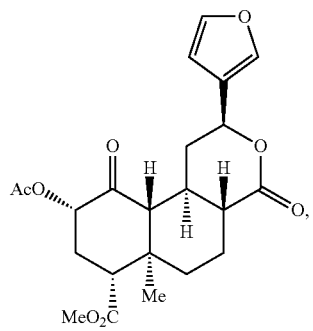

or as shown in perspective view:

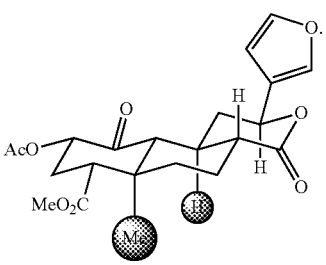

It may be noted that the 20-substituent, methyl in the natural product and hydrogen in the nor-20 analog synthesized herein, occupies a prominent axial position on the molecular skeleton.

The present invention provides, for the first time, the compound 20-nor-salvinorin A. Further, in various embodiments, synthetic procedures and intermediates previously unknown that can yield 20-nor-salvinorin A.

The invention further provides, in various embodiments, methods of modulating a kappa-opioid receptor, and methods of treatment medical conditions that indicate therapeutic modulation of a kappa-opioid receptor. The medical condition can comprise pain, pruritis, depression, or inflammation, or conditions implicating perception and consciousness. In various embodiments, the 20-nor-salvinorin is less addictive to the patient during the course of the treatment than is a modulator of a mu-opioid receptor. Further, in various embodiments, the 20-nor-salvinorin A compound is more stable chemically than is salvinorin A.

DETAILED DESCRIPTION

In the last decade, lethal opioid overdose rates have doubled in the United States. The number of opioid-related deaths in 2015 surpassed 33,000, which rivaled U.S. motor vehicle fatalities (35,000); preliminary estimates from 2016 showed the annual rate continuing to rise. To counter this epidemic, replacement of abused opioids with alternate pain therapeutics has emerged as an increasingly sensible goal. One alternative antinociceptive target under investigation is the kappa-opioid receptor (κ-OR), a G protein-coupled receptor (GPCR) that is expressed throughout the nervous system and modulates consciousness, cognition, mood and pain. κ-OR-targeted analgesic development has focused on chemical property modification to generate peripherally-restricted κ-OR agonists that lack central nervous system (CNS)-associated effects (e.g. hallucination), or that promote biased signaling to minimize β-arrestin-associated effects (e.g. sedation, dysphoria). Among the more potent and selective agonists of the κ-OR is the brain-penetrant plant metabolite salvinorin A (SalA), which was identified as the primary psychoactive principle of *Salvia divinorum* and the most potent naturally-occurring hallucinogen ever discovered. As a result, SalA has been subject to semi-synthetic modification and total synthesis to adjust its chemical properties and/or promote biased signaling of the κ-OR. Notably, a thiocyanate analog of SalA, RB-64, was shown to strongly bias towards G protein-coupled signaling. While many semi-synthetic analogs of SalA have been explored, the most prolific investigators recently noted that its "chemical liabilities . . . narrow the available pool of viable chemical transformations".

For example, both semi-synthesis and total synthesis encounter the configurational lability of the C8 carbon, which undergoes epimerization to a lower affinity isomer, 8-epi-SA (154-356-fold loss in potency). The reaction mechanism has been hypothesized to involve either ring-fragmentation/reclosure or simple enolization/reprotonation, with the bulk of evidence pointing to the latter. However, the driving force for this trans- to cis-ring fusion has not been identified. We believed a combination of lactone planarity and C20 axial-strain to be responsible. Analogy can be drawn to bridgehead (C10) methyl substitution of 1-decalone, which alters its trans:cis equilibrium ratio from 95:5 (C10-H) to 59:41 (C10-Me), driven by relief of the Me-C3-$H_{ax}$ 1,3-diaxial interaction in the cis-isomer. In order to stabilize the scaffold and attenuate epimerization, C20 of SalA might be resected through chemical synthesis, whereas semisynthetic removal would be difficult. The effect of this modification on the chemical synthesis itself is profound.

Figure 1:
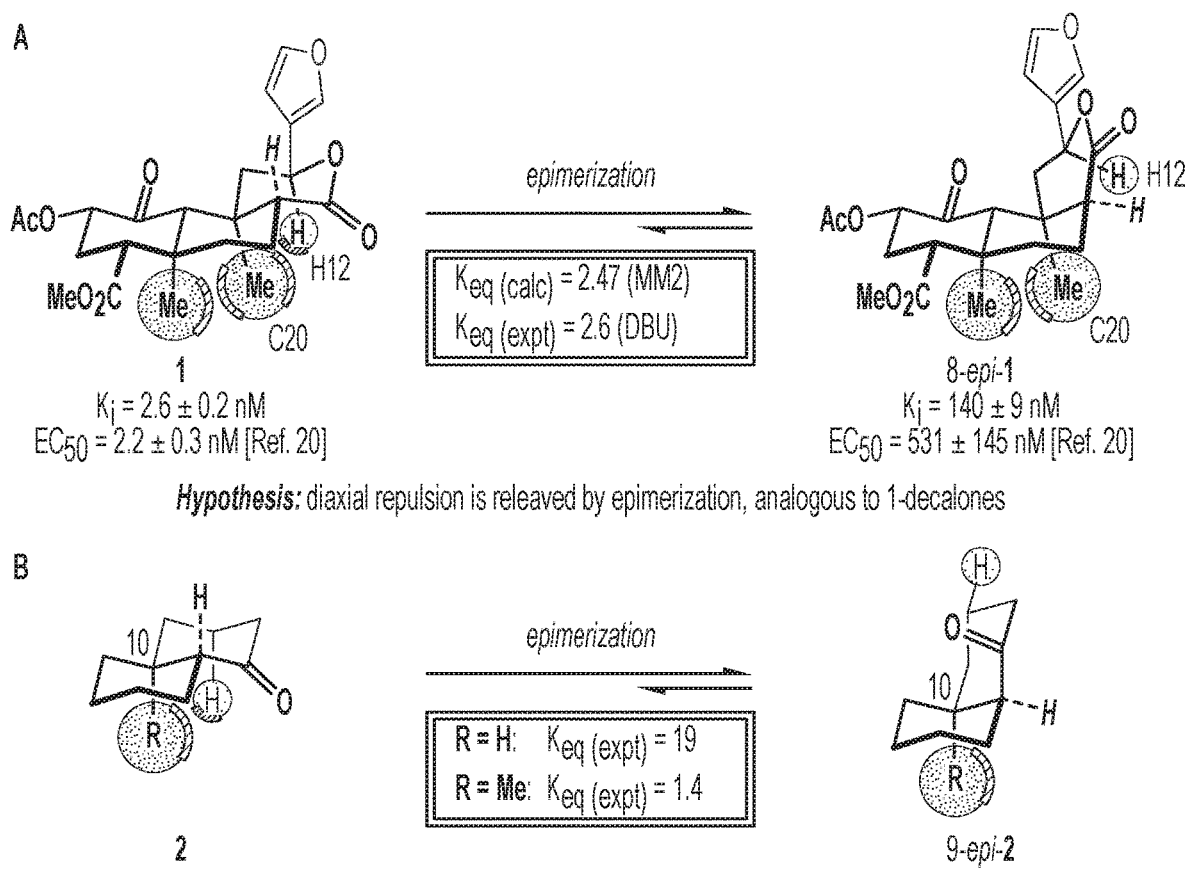
FIGS. 1A, 1B. Chemical instability of SalA. (A) Calculation predicts and experimentation shows that SalA is disfavored to 8-epi-SalA by 1:2.5 and 1:2.6 ratios at 25 and 80° C., respectively. This epimerization leads to significant loss in potency. B. We hypothesized that the driving force for this epimerization is partly diaxial repulsion between C20 and H8, which is relieved in the cis-fused isomer, analogous to 10-methyl-1-decalone epimerization. Therefore, like 1-decalone, C20 (methyl) deletion should stabilize the SalA scaffold.
Figure 2:
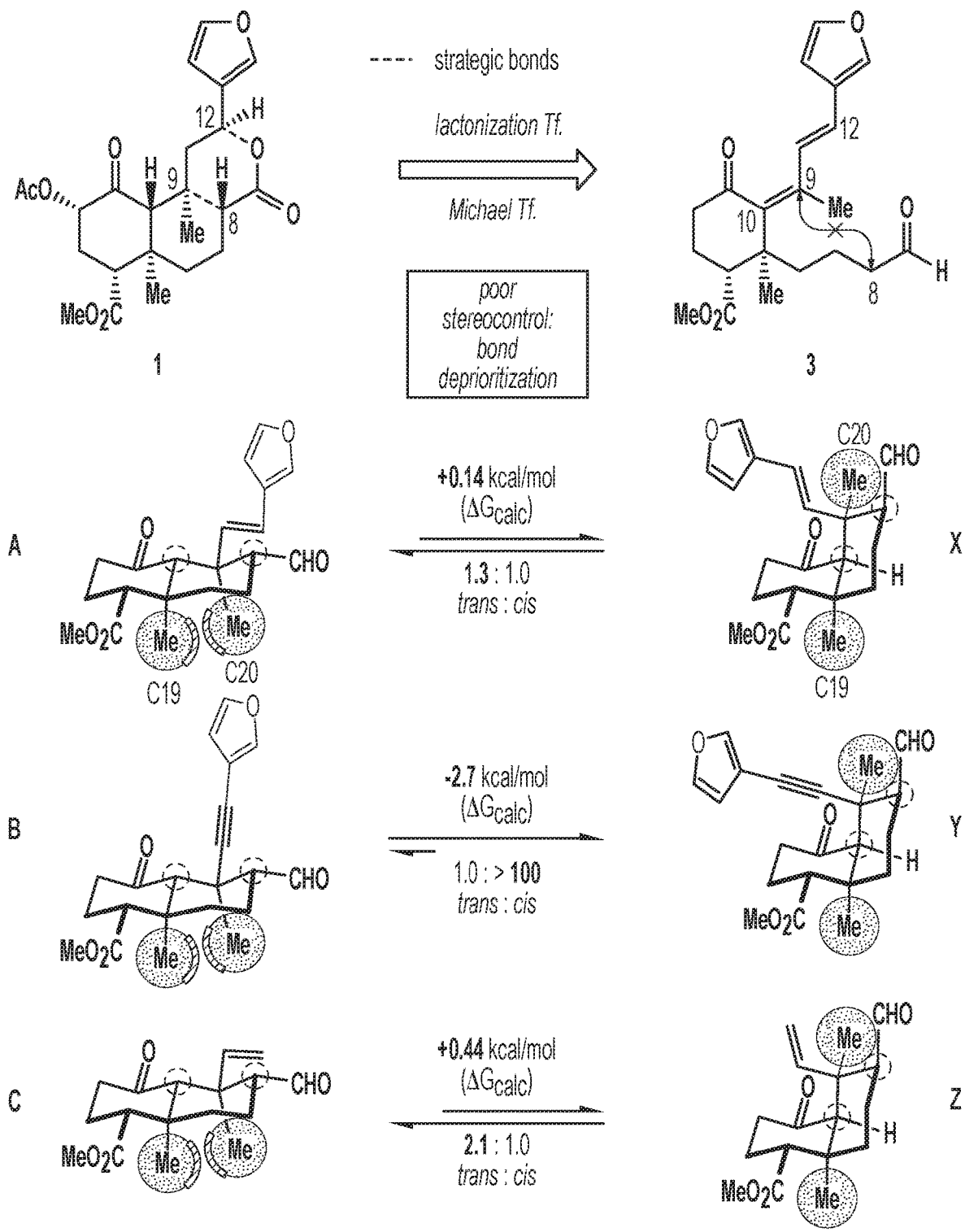
FIG. 2. Retrosynthetic analysis of 1 using strategic bond analysis. In addition to SalA scaffold destabilization, C20 destabilizes intermediate decalones and thus deprioritizes a key strategic bond (C8-9). C20 also frustrates precursor synthesis as a substituent on a tert-alkyl tetrasubstituted alkene.

When strategic bonds (SBs) in SalA are considered, the C20 (methyl)-bearing quaternary carbon (C9) becomes important. Two SBs in SalA take priority over other possibilities through the large reduction of complexity associated with their cleavage: a C12-O lactonization transform removes a heteroatom bond, ring and stereocenter, and a C8-9 Michael transform removes a ring and 3 stereocenters, leaving a simple cyclohexanone. However, strategic prioritization of the C9-10 bond ignores stereocontrol, which suffers from the small potential energy calculated to separate sub-targets A-C from stereoisomers X-Z. As a result of the diaxial C19/C20 methyls, A and C only favor the desired trans-decalone by a slim margin, and alkyne B heavily favors the cis-decalone Y. Notably, the four prior total syntheses avoid decalone intermediates altogether, despite their simplicity. Furthermore, precursor 3 contains a tetrasubstituted alkene (C9=10) in which one substituent is a quaternary carbon. See FIGS. 1-3.

These problems abate if the target is treated not as static but as dynamic. The C9-10 bond becomes strategic for disconnection only by resection of the C20 methyl; C9-10 can be considered a 'dynamic strategic bond.' Three benefits emerge. First, the intermediate trans-decalin is calculated to predominate over the cis-isomer, in contrast to A-C vs. X-Z. Second, the unsaturated cyclohexanone precursor would arise from condensation of a β,β-disubstituted cyclohexenolate with an aldehyde instead of a methyl ketone: the latter is a challenging reaction for which we found no precedent. Third, 20-nor-SalA is calculated to be more stable than its C8-epimer, reversing the configurational preferences of SalA itself. Taken together, there is only one reason not to resect C20: 20-nor-SalA is an unknown molecule with unknown binding affinity to the κ-OR.

Figure 4:
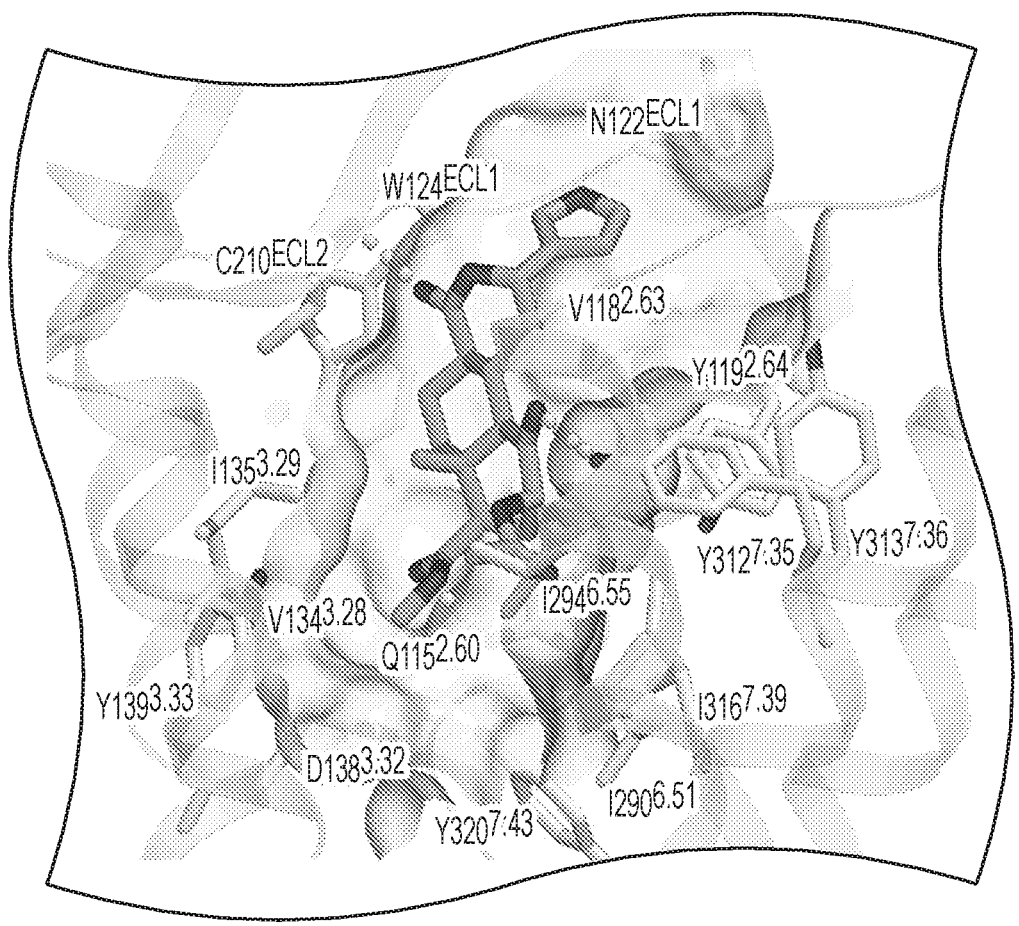
FIG. 4. Calculated binding to the κ-OR. The ligand, 20-nor-SalA, is shown in an orange colored stick representation inside the receptor (purple colored cartoon representation). Residues in the ligand vicinity are shown in white colored stick representation, and associated hydrogen bonds are shown in yellow colored dots.

The prospect of undertaking a total synthesis of a complex molecule for application opioid receptor pharmacology with no guaranteed target affinity was daunting. So, we first explored the binding of 20-nor-SalA to the κ-OR in silico. However, the recent crystal structure of a κ-OR with antagonist JDTic reflects an inactive state conformation of the binding pocket, specific to JDTic, and therefore is not well suited for binding of agonist SalA or its analogs. Therefore, we developed an active-like model of the κ-OR by using homology modeling based on an active state agonist-bound crystal structure of the mu-opioid receptor (MOR) (PDB ID: 5c1m). Receptor modeling included thorough sampling and optimization of the binding pocket side chains. The resulting active-like KOR receptor model was used to dock SalA and nor-20-salA using all-atom global energy optimization algorithm, based on Monte Carlo sampling of the ligand and residue sidechains within 4 Å of the ligand. In the predicted docking models SalA and 20-nor-salA bind in similar poses and with comparable binding scores (−20.2 and −18.43, respectively). In this binding pose nor-20-salA forms polar interactions with $Q115^{2.60}$, $Y312^{7.35}$, $C210^{ECL2}$ and, potentially, $N122^{ECL1}$ side chains. The ligands also make hydrophobic interactions with $Y119^{2.64}$, $Y313^{7.36}$, $I294^{6.55}$, and $V118^{2.63}$ residues. This pose also satisfies the ligand interaction contacts derived from mutagenesis data for SalA. In this pose, the 20-methyl group is directed towards the extracellular region with no apparent interactions with the receptor. This binding pose suggested comparable binding affinity for SalA and its nor-20 derivative. See FIG. 4.

These calculations provided a theoretical basis for investigation; justification for total synthesis usually depends on experimentally observed activity. However, knowledge of κ-OR affinity in this case required synthesis—a catch-22. A study to probe structure-activity relationships in SalA could not reach the nor-20 target, so no empirical data was available. Nevertheless, we felt the potential benefits for therapeutic development outweighed the risk. Furthermore, the simplification imparted by C20 resection significantly improved material access by unlocking the C9-10 bond, whereas prior syntheses of SalA produced only small amounts of late-stage material over multiple operations (20-29 steps; 0.7-1% yield).

The synthesis (see Schemes 1A and 1B, below) commenced from Hagemann's ester (S1), a commercially available building block common in terpene synthesis, which appeared to be an obvious precursor to 20-nor-SalA via vicinal difunctionalization. Grignard reagent S3 was generated from commercially available tert-butyl(4-chlorobutoxy)dimethylsilane and used directly. However, early experiments to trap the sterically-encumberred enolates resulting from conjugate addition proved fruitless, even with the simplest electrophiles like acetaldehyde. Enolate transmetallation with diethylzinc allowed enol silane formation and Mukaiyama aldol addition, but always in low yield and never with electron-rich aldehydes. Instead, we found that addition of zinc chloride and five equivalents of acrolein resulted in efficient formation of S4 as an inconsequential 6:1 mixture of allylic alcohols. Elimination of this alcohol was effected by mesylation, followed by ketone enolization by addition of DBU. These conditions initially delivered a mixture of (E)- and (Z)-dieneones, but isomerization mediated by reversible DBU addition occurred with prolonged reaction time to favor (E)-S5 with 20:1 selectivity.

Subsequent steps for elaboration to 20-nor-salvinorin A involved careful choreography of 1) cyclization, 2) α-acetoxylation, 3) aryl appendage and 4) lactonization steps, based on extensive reconnaissance briefly discussed here. An initial Heck arylation of S5 with 3-bromofuran or its boronic esters proved low yielding and β-(3-furyl)-substitution lowered the electrophilicity of the dienone towards nucleophiles. Several ketone α-hydroxylations competitively oxidized the furan ring if present, and Hagiwara's conditions for acetate installation by Mitsunobu stereoinversion were inefficient and required purification from 20 equivalents $PPh_3$ and 10 equivalents diisopropyl azodicarboxylate. The aldehyde, not carboxylic acid oxidation state, was chosen to engage in Michael addition due to its ease of enolization (or enamine formation) in the presence of the two other enolizable carbonyls.

As a result, the final sequence involved tert-butyldimethylsilyl removal with 2 M HCl to yield S6, followed by Swern oxidation of the deprotected alcohol to aldehyde S7. Intramolecular Michael addition was carried out from the corresponding pyrrolidine enamine in methanol/tetrahydrofuran with added acetic acid. As the alcoholic co-solvent increased in size, the ratio of trans- and cis-decalone increasingly favored the undesired cis-decalin. Quench by potassium carbonate served to equilibrate an initially low ratio of trans-/cis-decalones to predominantly one isomer S8 (cis-decalone lower than 5% content by crude $^1$H NMR), which contained the contiguous stereopentad found in the salvinorin A scaffold. Substitution of alcohol co-solvent to ethanol resulted in a dramatically slower equilibration. Pinnick oxidation of aldehyde S8 capped a facile route to diversifiable carboxylic acid (S9), which was successfully scaled to 5.3 grams in a single pass. After much experimentation, we found only 4 steps to separate (S9) from 20-nor-SalA, affording a convenient platform for eventual diversification to alter the chemical properties of the SalA chemotype.

The first two of these steps address appendage of the equatorial acetate, which is challenged by the high selectivity for axial approach of electrophiles, the difficulty of $S_N2$ stereoinversion of these axial α-hydroxy and α-bromo cyclohexanones, and the high oxidation potential of furanyl intermediates. In some cases, α-debromination by acetate outcompeted substitution. These problems were solved by deprotonation of S9 with 2.1 equivalents of LDA followed by Davis oxaziridine addition, which generated in high diastereoselectivity the axial α-hydroxy-decalone S10. Subsequent acetylization occurred at both the alcohol and the carboxylic acid; warming this reaction mixture led to equilibration to favor the equatorial acetate without affecting the stereochemistry at any other position. Careful aqueous workup was performed to decompose the mixed anhydride at high pH and recover the carboxylic acid at low pH, while sparing the acetate S11 from cleavage during these operations.

The carboxylic acid itself was found to be crucial for the Heck arylation with 3-bromofuran. Early experiments to arylate the electronically unbiased olefin of aldehyde S8 surveyed a range of palladium sources, oxidants, ligands, solvents and bases, under both oxidative and traditional Heck conditions with little success. The optimal results in these early versions of the synthesis required ten portionwise additions of palladium(II) acetate, 3-furanylboronic acid, and a bifluoride source. Ultimately, the yield, reproducibility and enthusiasm for this intensive procedure were low. Fortunately, we discovered that carboxylic acids S10 or S11 (in contrast to aldehyde S8) underwent very efficient Heck arylation as their alkali salts: the potassium carboxylate provided the highest yields of S12 and XPhos ligands promoted the highest rates and catalyst turnovers. The superiority of carboxylic acids to the corresponding aldehyde may derive from accelerated coordination/migratory insertion by initial coordination of the 3-furyl-palladium(II) by the potassium carboxylate. Analogy can be drawn to classic proximity effects recently brought to bear in palladium catalysis using carboxylic acids. To the best of our knowledge, the closest precedent in the Heck reaction of haloarenes involves the accelerated arylation of unsaturated primary amides compared to their corresponding phthalimides.

The final obstacle to 20-nor-salvinorin A required lactonization of the carboxylic acid onto an electron-rich conjugated alkene with Markovnikov regioselectivity and equatorial stereoselectivity—on its face an uncomplicated scenario. We were therefore dismayed to discover that subjection of S12 to a variety of Brønsted acids led to furan decomposition at rates competitive with lactonization, and what little lactones could be recovered were equimolar mixtures of diastereomers at C12.

The same lactones were generated in trace quantities by the Heck reaction (S11→S12), possibly by a Pd—H-mediated pathway, but never in preparatively useful yields, nor with stereoselectivity. Experimentation with radical-polar crossover cyclization and Lewis acid-assisted cyclization honed in on Bi(OTf)$_3$ in hexafluoroisopropanol (HFIP) solvent as the highest yielding conditions that exhibited good rates (61%, $t_{1/2}$=30 mins at 0° C.), but no stereoselectivity. We were surprised to find that solutions of S12 in HFIP in the absence of any Lewis acids underwent lactonization, albeit with substantially decreased rates ($t_{1/2}$=3.5 days at 40° C.), these were the only conditions to exhibit stereochemical preference for 20-nor-salvinorin A (4:1 d.r. @ 60% conversion). Neither trifluoroethanol (TFE, pKa=12.4) nor nonafluoro-tert-butanol (pKa=5.2) promoted efficient lactonization, even at elevated temperature (90° C.), highlighting the idiosyncracy of HFIP (pKa=9.3), which likely acidifies the carboxylic acid via a hydrogen bonding network unavailable to other flourous alcohols [REF]. The lactonization is reversible in HFIP: at elevated temperatures 20-nor-salvinorin A equilibrates to S12 and 12-epi-20-nor-salvinorin A with no stereoselectivity. Therefore, the stereoselectivity observed at lower temperatures is kinetic and likely derives from an internal protonation and collapse of the ion pair. For preparative purposes, we have found it easiest to generate 20-nor-salvinorin A with high conversion from S12, but with low stereoselectivity since 12-epi-20-nor-salvinorin A is easily separable. Alternatively, we can halt the reaction at low conversion and good stereoselectivity, which may be useful for analogs whose diastereomers are inseparable.

We proposed 20-nor-salvinorin A as a novel kappa opioid receptor (KOR) agonist based on the known plant metabolite salvinorin A (SA). Deletion of the C20 (methyl) group stabilizes the natural, potent C8 configuration and also allows the molecule to be accessed in a short chemical synthesis. The chemistry will allow many analogs to be prepared on any scale. We devised and executed a 10 step synthesis that allows for diversification at multiple points and incorporation of deep-seated changes to modify chemical properties and pharmacological profile.

Pain, pruritis, depression, inflammation, and conditions implicating perception and consciousness are among the medical conditions that can be treated with this novel molecule: use of the compound can provide non-addictive therapeutics in these areas.

C20-Me deletion stabilizes the SA scaffold. SA and its analogs have been targeted as non-addictive analgesics. In the past, SA has been difficult to modify because its instability 1) obstructed semi-synthesis from plant extracts and 2) complicated de novo synthesis. Our chemical synthesis of our novel analog (nor-20-SA) allowed confirmation that it agonizes the KOR with high potency, similar to know KOR agonist U69,593. We now have the ability to generate diverse analogs.

Figure 5:
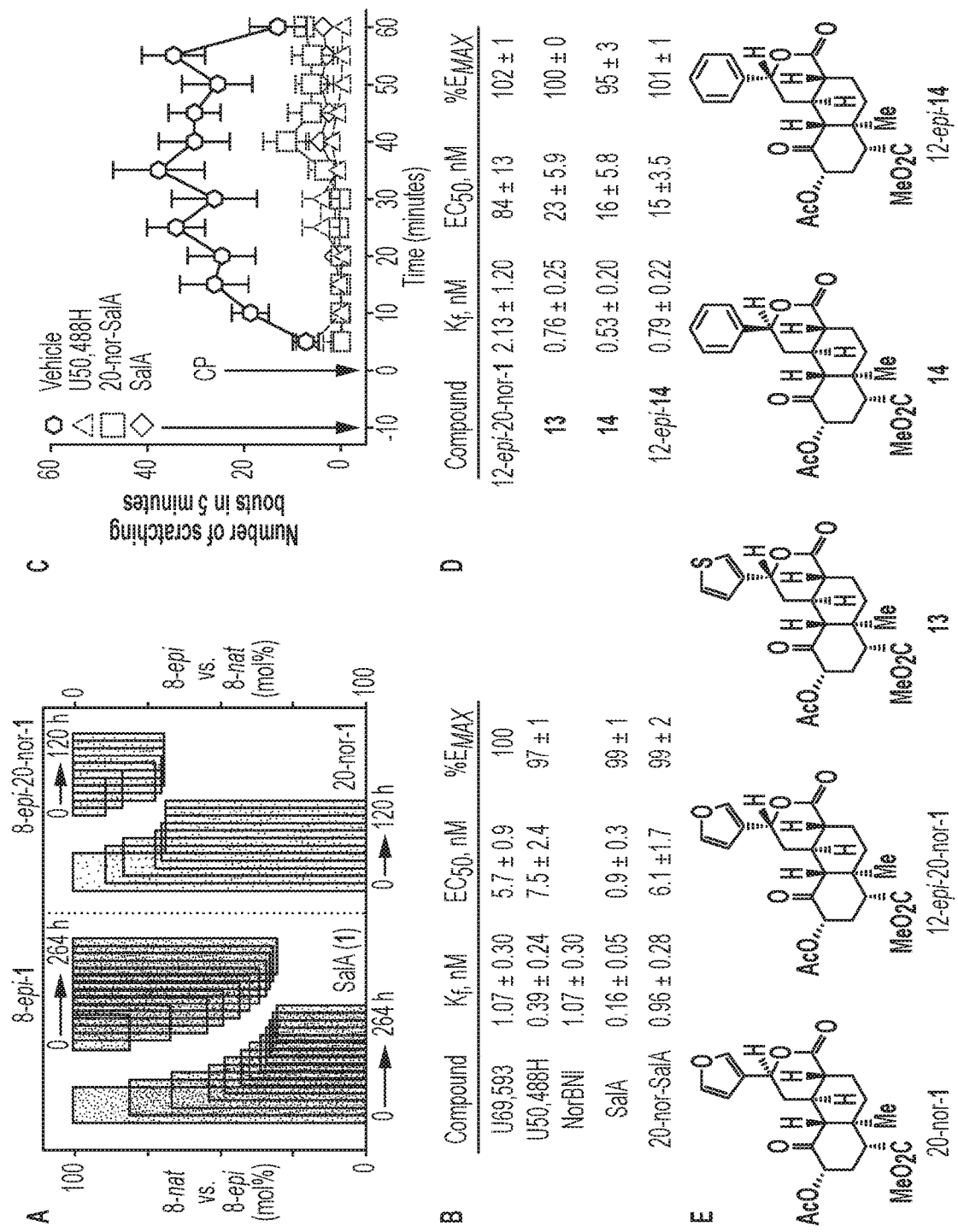
FIGS. 5A, 5B, 5C, 5D, 5E. Comparison of chemical reactivity and biological activity. (A) Treatment of salvinorin A and 20-nor-salvinorin A with DBU in $d_3$-MeCN at 80° C. results in slow epimerization at C8. However, salvinorin A isomerizes to favor 8-epi-salvinorin A, whereas 20-nor-salvinorin A is more stable than its C8 epimer. (B) Affinity and functional signaling parameters at the human KOR expressed in CHO-K1 cells. Radioligand competition binding assays were preformed against 3H-U69,593 to determine $K_i$ (n=3-9). Inhibition of cAMP accumulation was used to determine $EC_{50}$ and $E_{MAX}$ values by nonlinear regression analysis (n=6-8). Data are shown as the mean±SEM. (C) Kappa agonists suppress chloroquine phosphate-induced pruritus in mice. Chloroquine phosphate (CP 40 mg/kg, s.c.) was administered 10 minutes following a 3 mg/kg, (s.c.) injection of each compound and scratching behaviors were monitored over time. All compounds suppressed the itch response at this dose over time compared to vehicle (1:1:8, DMSO: Tween 80: 0.9% sterile saline) pretreatment (interaction of time and drug: $F_{(36, 234)}=14.59$, p<0.0001, 2-way ANOVA (n=9 vehicle, 5 U50, 5 20-nor-SalA, 3 SalA). (D) identical to B. (E) Analogs synthesized using the same final steps in Scheme 1B.

Complete stereoselective total synthesis has been executed multiple times to produce multiple milligram quantities of target compound and its analogs. The novel ligands show high KOR affinity (see FIG. 5).

Figure 3:
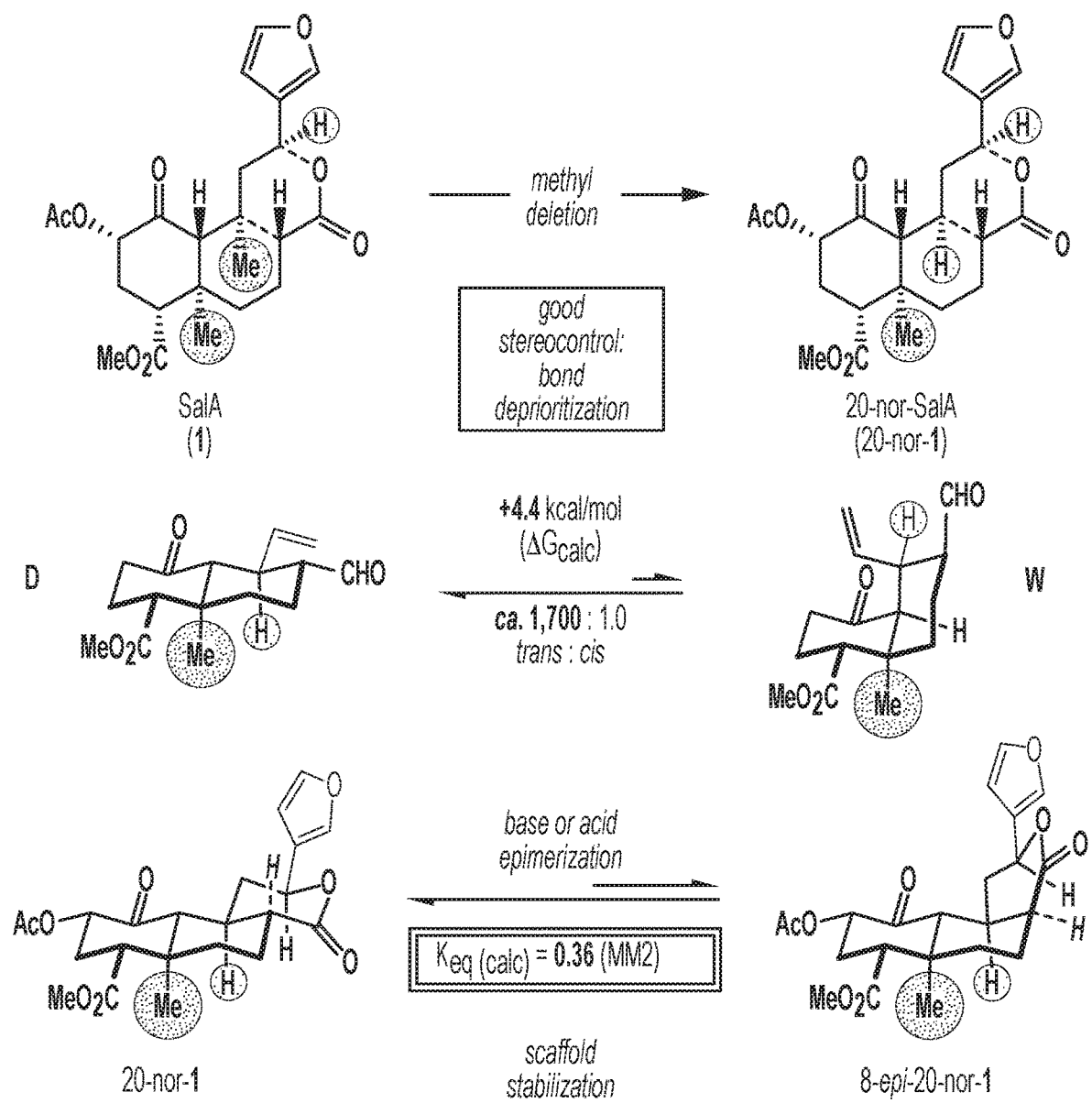
FIG. 3. Treatment of SalA as a dynamic structure unlocks the C9-10 strategic bond (SB) for Michael transform by C20 deletion. Both decalone intermediates and the SalA scaffold itself is stabilized. The Michael reaction precursor becomes very easy to synthesize.

Access to 20-nor-salvinorin A allowed us to compare its chemical reactivity and biological activity to salvinorin A. As reported by multiple investigators, SalA is undergoes epimerization under basic conditions to disfavor the natural configuration at C8. Similarly, we found 0.5 equivalents of DBU in d$_3$-acetonitrile to generate a 28:72 mixture of salvinorin A:8-epi-salvinorin A at 80° C. (Scheme 1B). In contrast, this relative stability is nearly reversed in 20-nor-SalA: under identical conditions the equilibrium holds at 68:32, very close to the calculated K$_{eq}$ (FIG. 3). More importantly, 20-nor-SalA retains high affinity for the κ-OR, as measured by radioligand competition binding against [$^3$H]-U69,593. It also behaves as a full agonist in G protein signaling assays measured by the inhibition of forskolin-stimulated, adenylyl cyclase-mediated, cAMP accumulation. The pharmacological properties of 20-nor-SalA closely match the conventional, selective agonist U69,593, although SalA has slightly higher affinity and efficacy than either (FIG. 5B). While we consider our chemical synthesis to be more useful for scaffold diversification than for large-scale production, its brevity has allowed us to prepare enough material (>75 mg) to test for antipruritic properties in animals. κ-OR agonists suppress non-histamine-related itch in rodents and in humans, so we evaluated the ability of 20-nor-salvinorin A to suppress itch in mice, and found it similarly effective to SalA and another conventional agonist (U50,488H) (FIG. 5C) indicating a functional equivalence.

Preliminary proof-of-principle for the generality of this route, especially the late stage carboxylate-accelerated Heck reaction and alkene lactonization, was established by the synthesis of aryl analogs that have been inaccessible by semi-synthetic modification of isolated salvinorin A (FIG. 5D). For example, a thiophene has never been substituted for the naturally-occurring furan, as in 13, which exhibits relatively high affinity but reduced efficacy. And while cycloaddition of dimethylacetylene dicarboxylate with 1 has been used to replace the furan with disubsituted phenyl rings, 31-39 fold losses in binding affinity were observed. In contrast, we found that purely unsubstituted phenyl analogs of 20-nor-1 retain the same binding affinity as their furyl counterparts, even the C12-epimer 14. Thus, a small handful of analogs has already opened opportunities for scaffold alteration, and this information should aid the design of analogs with modified physical properties.

As demonstrated here, the integration of dynamic retrosynthetic analysis with in silico docking can advance the use of complex secondary metabolites (natural products) as drug leads. The complexity of many secondary metabolites has been embraced as a useful entry into diverse and privileged chemical space. However, complexity is also a recognized obstacle, prompting scaffold redesign to bypass arduous synthesis campaigns while retaining target affinity. In contrast, we hope to use the approach demonstrated here—calculated affinity/dynamic retrosynthetic analysis—to minimally perturb complexity and affinity, only enough to reveal the most efficient retrosynthetic path. A docking program coupled to traditional retrosynthesis search algorithms might easily be deployed against many complex metabolites with known targets. Although restricted to a single illustration here, this approach has proved successful for the salvinorin chemotype of κ-OR agonist. By deletion of a single methyl group, we have simultaneously stabilized the salvinorin scaffold and simplified its synthesis, while maintaining target engagement. This chemical platform is capable of generating analogs that have been inaccessible by semisynthesis, and which also retain high potency. Further modification of the nor-20-SalA scaffold will focus on improvement of half-life in blood, bioavailability (peripheral restriction) and bias against parrestin recruitment, as well as further scaffold stabilization. Success in these goals should deliver multiple candidates for next generation analgesics.

Schemes 1A and 1B, below, separated for clarity, together show an embodiment of the synthetic route used in the present invention.

BACKGROUND DOCUMENTS

B. L. Roth et al. *Proc. Natl. Acad. Sci. U.S.A.* 2002, 99, 11934-11939.
T. E. Prisinzano, R. B. Rothman, *Chem. Rev.* 2008, 108, 1732-1743.
R. C. Stevens, et al. *Nature* 2012, 485, 327-334.
A. M. Sherwood, *J. Med. Chem.* 2017 60, 3866-3878.
J. R. Scheerer, J. F. Lawrence, G. C. Wang, D. A. Evans, *J. Am. Chem. Soc.* 2007, 29, 8968-8969.
M. Nozawa, Y. Suka, T. Hoshi, T. Suzuki, H. Hagiwara, *Org. Lett.* 2008, 10, 1365-1368.
H. Hagiwara, Y. Suka, T. Nojima, T. Hoshi, T., T. Suzuki, *Tetrahedron* 2009, 65, 4820-4825.
N. J. Line, A. C. Burns, S. C. Butler, J. Casbohm, C. J. Forsyth, *Chem. Euro. J.* 2016, 22, 17983-17986.
E. J. Corey, W. J. Howe, H. W. Orf, D. A. Pensak, G. Petersson *J. Am. Chem. Soc.* 1975, 97, 6116-6124.
E. J. Corey, A. K. Long, S. D. Rubenstein *Science* 1985, 228, 408-418.

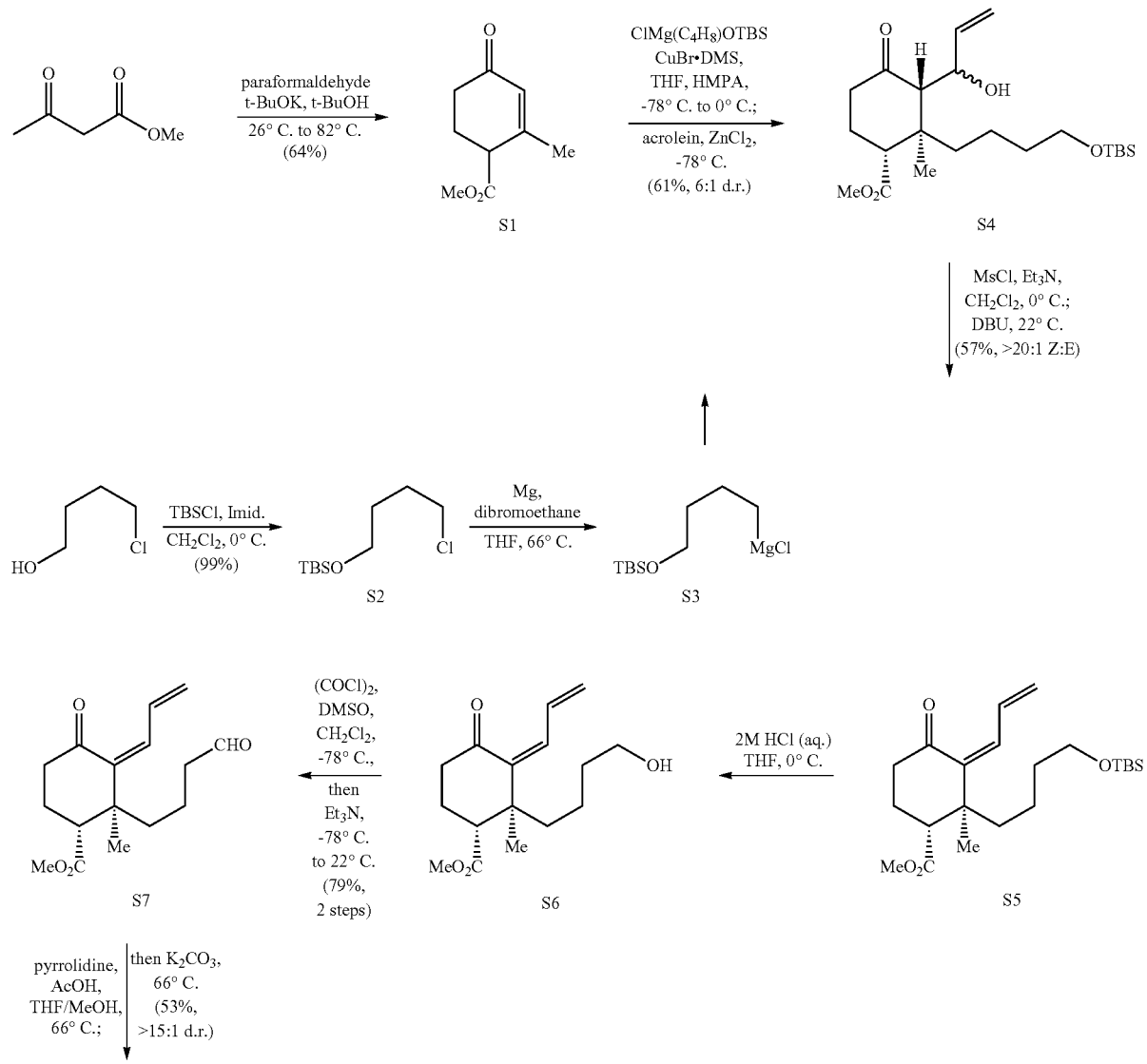

Scheme 1A

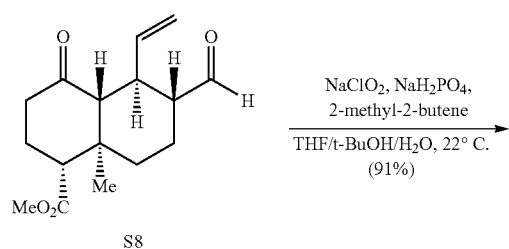 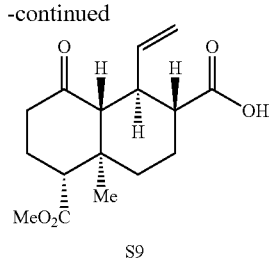 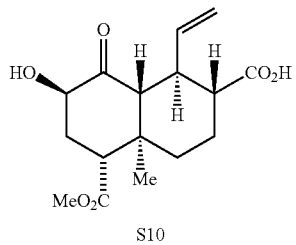
Scheme 1B
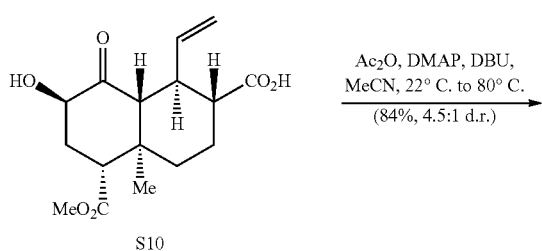 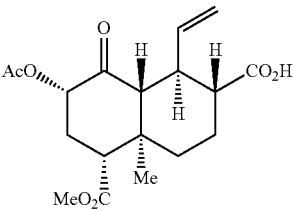 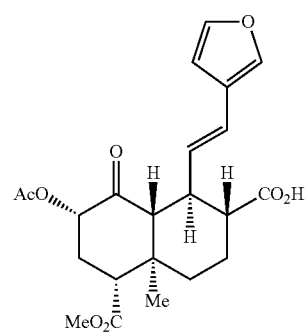

-continued

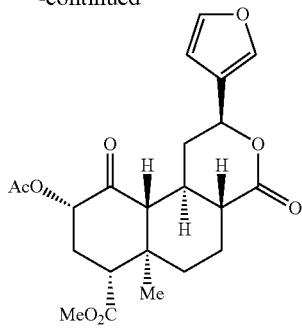

20-nor-salvinorin A

In various embodiments, the invention provides, as a composition of matter per se, a compound of formula 20-nor-salvinorin A:

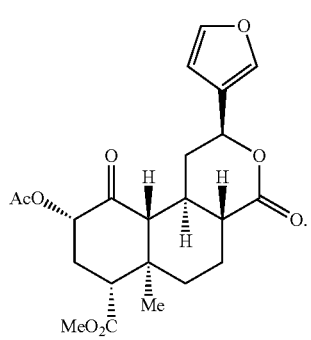

20-nor-salvinorin A

The invention further provides a pharmaceutical composition comprising 20-nor-salvinorin A and a pharmaceutically acceptable excipient.

In various embodiments, the invention provides a method of modulating a kappa-opioid receptor, comprising contacting the kappa-opioid receptor with an effective amount or concentration of 20-nor-salvinorin A.

The invention further provides, in various embodiments, a method of treating a medical condition in a patient, wherein modulation of a kappa-opioid receptor is medically indicated, comprising administering to the patient an effective dose of 20-nor-salvinorin A. For instance, the medical condition can comprise pain, pruritis, depression, or inflammation, or conditions implicating perception and consciousness. The 20-nor-salvinorin A can be less addictive to the patient during the course of the treatment than a modulator of another type of opioid receptor, such as a modulator of a mu-opioid receptor or a delta-opioid receptor. Furthermore, the 20-nor-salvinorin A can be more stable chemically than salvinorin A.

An effective and practical synthesis of 20-nor-salvinorin A can be achieved using the synthetic intermediates and procedures herein. It is apparent to the person of ordinary skill that reaction conditions, e.g., temperature and time, can be varied to a reasonable extent to provide comparable results to the specific reaction conditions described and claimed herein.

For instance, the invention provides, as a composition of matter per se, a compound of formula S12

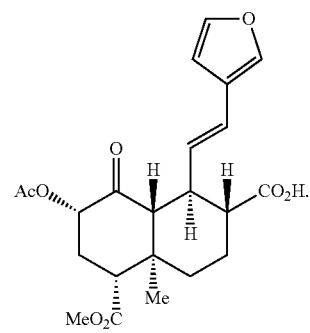

S12

This synthetic intermediate, prepared as described in the following disclosure, can be used as a precursor in a method of synthesis of 20-nor-salvinorin A, comprising contacting a compound of formula S12 and anhydrous 1,1,1,3,3,3-hexafluoropropan-2-ol at 100° C.

The invention further provides, as a composition of matter per se, a compound of formula S11

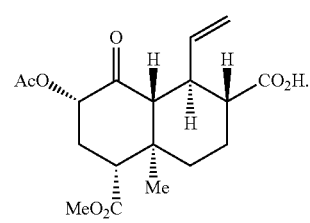

S11

This synthetic intermediate, prepared as described in the following disclosure, can be used as a precursor in a method of synthesis of the compound S12,

S12

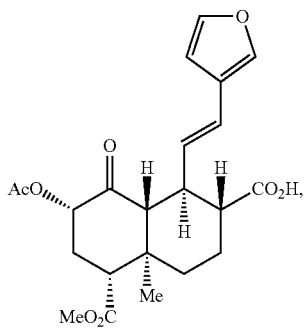

comprising contacting compound S11 and 3-bromofuran in the presence of Pd(OAc)$_2$ (10 mol %), XPhos (20 mol %), and K$_2$CO$_3$ in DMF, at 80° C.

The invention also provides, as a composition of matter per se, a compound of formula S10

S10

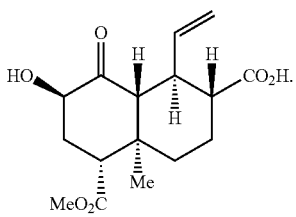

This synthetic intermediate, prepared as described in the following disclosure, can be used as a precursor in a method of synthesis of the compound S11

S11

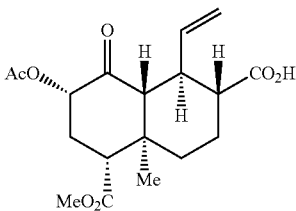

comprising contacting compound S10 and Ac$_2$O, DMAP, DBU, in MeCN, at 22° C. to 80° C.

The invention also provides, as a composition of matter per se, a compound of formula S9

S9

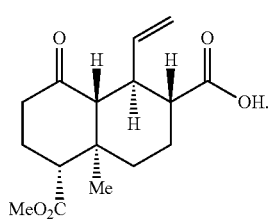

This synthetic intermediate, prepared as described in the following disclosure, can be used as a precursor in a method of synthesis of the compound of formula S10

S10

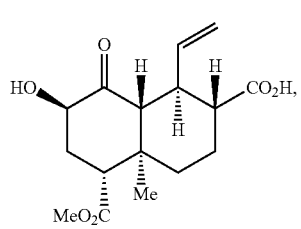

comprising contacting compound S9 and LDA in THF at −78° C.; then with Davis' oxaziridine.

The invention further provides, as a composition of matter per se, a compound of formula S8

S8

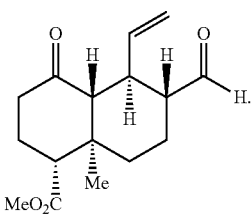

This synthetic intermediate, prepared as described in the following disclosure, can be used as a precursor in a method of synthesis of the compound of formula S9

S9

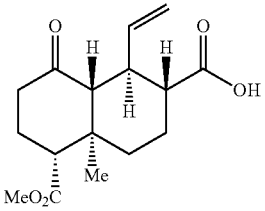

comprising contacting compound S8 of claim 16 and NaClO$_2$, NaH$_2$PO$_4$, and 2-methyl-2-butene in THF/t-BuOH/H$_2$O, at 22° C.

The invention also provides, as a composition of matter per se, a compound of formula S7

S7

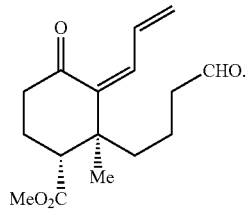

This synthetic intermediate, prepared as described in the following disclosure, can be used as a precursor in a method of synthesis of the compound of formula S8

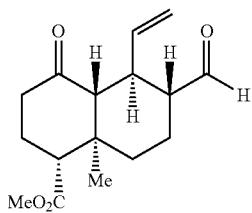

comprising contacting a compound of formula S7 and pyrrolidine, and AcOH, in THF/MeOH, at 66° C.; then with K₂CO₃, at 66° C.

Taken in sequence, the invention further provides, in various embodiments, a method of synthesis of 20-nor-salvinorin A, comprising:

(a) contacting a compound of formula S7

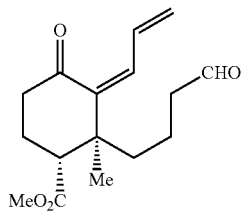

and pyrrolidine, and AcOH, in THF/MeOH, at 66° C.; then with K₂CO₃, at 66° C.; to yield a compound of formula S8

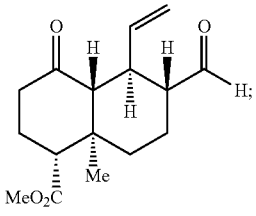

then, (b) contacting the compound of formula S8 and NaClO₂, NaH₂PO₄, and 2-methyl-2-butene in THF/t-BuOH/H₂O, at 22° C., to yield a compound of formula S9

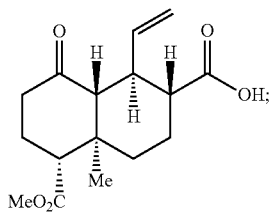

then, (c) contacting the compound of formula S9 and LDA in THF at −78° C.; then with Davis' oxaziridine, to yield a compound of formula S10

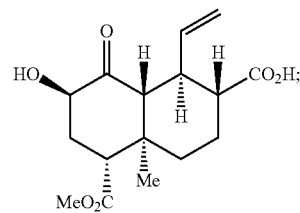

then, (d) contacting the compound of formula S10 and Ac₂O, DMAP, DBU, in MeCN, at 22° C. to 80° C., to a compound of formula S11

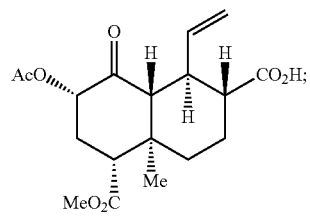

then, (e) contacting the compound of formula S11 and 3-bromofuran in the presence of Pd(OAc)₂ (10 mol %), XPhos (20 mol %), and K₂CO₃ in DMF, at 80° C., to yield a compound of formula S12

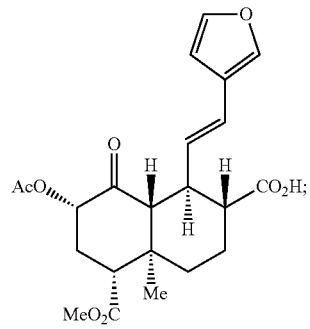

then, (f) contacting the compound of formula S12 and 1,1,1,3,3,3-hexafluoropropan-2-ol at 100° C., to yield 20-nor-salvinorin A

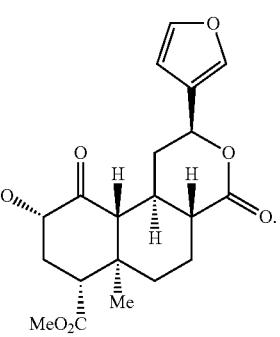

Suitable variations and modifications of these synthetic procedures are doubtless apparent to the person of ordinary skill, and are encompassed herein.

EXAMPLES

Abbreviations Used

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.
Other abbreviations used include:
AcOH acetic acid
Davis' oxaziridine:

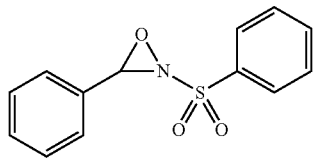 [SMILES: O=S(=O)(c1ccccc1)N1OC1c1ccccc1]

DBU diazabicycloundecane
DMAP 4-(N,N-dimethylamino)pyridine
DMF N,N-Dimethylformamide
DMS dimethylsulfide
DMSO dimethylsulfoxide
$Et_3N$ triethylamine
HMPA hexamethylphosphoramide
LDA lithium di-isopropylamide
MeCN acetonitrile
TBS t-butyldimethylsilyl
THF tetrahydrofuran
XPhos

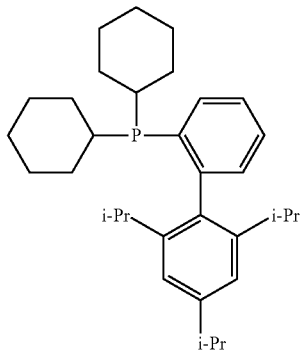 [SMILES: CC(C)c1cc(C(C)C)c(-c2ccccc2P(C2CCCCC2)C2CCCCC2)c(C(C)C)c1]

Materials and Methods.

All reactions were carried out under positive pressure of argon in a well-ventilated fume hood unless otherwise noted. Hexanes (ACS grade), ethyl acetate (ACS grade), toluene (ACS grade), and diethyl ether (anhydrous ACS grade) were purchased from Sigma-Aldrich and used without further purification. Dichloromethane (ACS grade), acetonitrile (ACS grade), chloroform (ACS grade), and isopropanol (ACS grade) were purchased from Fisher Chemical and used without further purification. Anhydrous tetrahydrofuran was purchased from Sigma-Aldrich and used without further purification. Anhydrous HMPA was distilled from calcium hydride (10% w/v) through a frit of steel wool under reduced pressure. Anhydrous triethylamine was purchased from Sigma-Aldrich and used without further purification. Anhydrous potassium carbonate was dried at 200° C. for at least 12 hours. Anhydrous DBU was distilled from calcium hydride (10% w/v) under reduced pressure. Anhydrous DMF was purchased from Sigma-Aldrich and used without further purification. Anhydrous hexafluoroisopropanol was stirred over calcium hydride (10% w/v) for 30 minutes, then distilled under positive pressure of argon. Anhydrous acetonitrile was distilled from phosphorus pentoxide (10% w/v) under positive pressure of argon. Anhydrous zinc chloride was dried by stirring at 150° C. under reduced pressure for several hours. Acrolein was distilled under reduced pressure and collected at −78° C. Anhydrous methanesulfonyl chloride was distilled from phosphorus pentoxide (10% w/v) under reduced pressure. 3-bromofuran was passed through a plug of neutral aluminum oxide. Anhydrous dichloromethane was distilled from calcium hydride (10% w/v) under positive pressure of argon. n-Butyllithium was titrated with a solution of recrystallized diphenylacetic acid in anhydrous tetrahydrofuran. Commercially available reagents were used without further purification unless otherwise noted. Reactions were monitored by thin layer chromatography (TLC) using precoated silica gel plates from EMD Chemicals (TLC Silica gel 60 F254). Flash column chromatography was performed over Silica gel 60 (particle size 0.04-0.063 mm) from EMD chemicals. GC/MS analysis was performed on Agilent 7820A/5975 GC/MSD system with helium as the carrier gas. 1H NMR and 13C NMR spectra were recorded on Bruker DPX-400 and Bruker DRX-600 (equipped with cryoprobe) spectrometers using residual solvent peaks as internal standard (CDCl3 @ 7.26 ppm 1H NMR, 77.06 ppm 13C NMR). Low resolution mass spectra were recorded on an Agilent 6120 Quadrupole LC/MS system with an ESI probe.
Experimental Procedures.

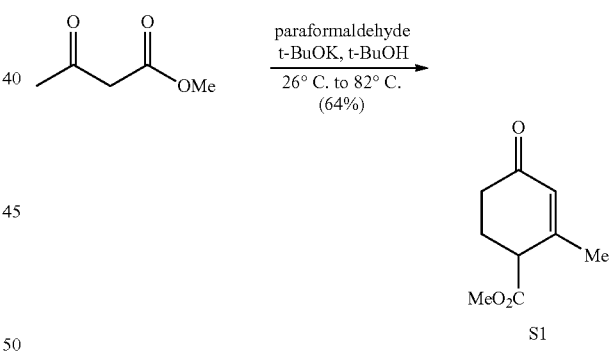

Hagemann Ester S1.

Methyl acetoacetate (85 mL, 788 mmol) was dissolved in tert-butanol (450 mL) and stirred with a magnetic stir bar at 26° C. (to ensure the solvent remained liquid). Paraformaldehyde (11.6 g, 386 mmol) was added to this solution in a single portion. To this colorless, opaque solution was added solid potassium tert-butoxide (4.4 g, 39.2 mmol) in portions, over ten minutes. The reaction was stirred at 26° C. for one hour; the reaction became faintly yellow. More solid potassium tert-butoxide (11.6 g, 103 mmol) was added in portions, over fifteen minutes. The reaction was heated to reflux for 12-18 hours. The yellow, opaque mixture was cooled to room temperature and concentrated in vacuo to less than 150 mL. Dichloromethane (200 mL) and 1 M hydrochloric acid (200 mL) were added, mixed well (a gas evolved), and the organic layer was separated. The aqueous layer was extracted with dichloromethane (2×100 mL), the organic fractions were combined and washed with brine. The organic layer was dried with magnesium sulfate, filtered, and concentrated in vacuo. The crude mixture was fractionally distilled at 4 torr; the fraction boiling from 79° C. to 82° C. was collected and weighed to 41.7 g (248 mmol, 64%).

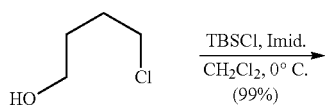

Silyl Ether S2.

Solid tert-butyldimethylsilyl chloride (137 g, 909 mmol) was dissolved in dichloromethane (800 mL) and stirred with a magnetic stir bar at 0° C. 85% 4-chlorobutanol (100 mL, 852 mmol) was added as a solution in dichloromethane (100 mL). The mixture was stirred at 0° C. for 30 minutes, followed by the addition of solid imidazole (71.3 g, 1048 mmol) in a single portion. This mixture was stirred at 0° C. until TLC indicated the alcohol was consumed, typically 1.5 hours. The reaction mixture was filtered through a medium glass frit, and the glassware was rinsed with dichloromethane. The filtrate was concentrated in vacuo, and the resulting translucent oil was stored at −20° C. for 12 hours. A colorless precipitate formed at this temperature. Hexanes (300 mL) was added, the suspension was passed through a Celite/MgSO₄ plug over a fine frit, and more hexanes (2×200 mL) was passed through the filter. The filtrate was concentrated in vacuo to give a colorless, transparent oil which weighed 189 g (848 mmol, 99%).

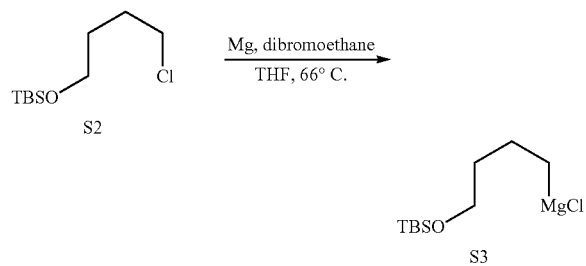

Grignard Reagent S3.

Magnesium turnings (11 g, 452 mmol) were suspended in anhydrous tetrahydrofuran (120 mL) and the mixture was stirred vigorously at 22° C. with a magnetic stir bar. Dibromoethane (2.2 mL, 25.5 mmol) was added in portions over ten minutes and the glassware was rinsed into solution with anhydrous tetrahydrofuran (10 mL). The mixture was stirred vigorously at reflux for 20 minutes, during which time a gas evolved. In a separate flask, alkyl chloride S2 (85.3 g, 383 mmol) was dissolved in anhydrous tetrahydrofuran (120 mL, ca. 230 total mL in solution). This alkyl chloride solution was added to the magnesium suspension portionwise over 30 minutes, and the glassware was rinsed with more anhydrous tetrahydrofuran (20 mL). The reaction was stirred vigorously at reflux for 5 hours, cooled to room temperature, then diluted with anhydrous tetrahydrofuran (120 mL). The remaining solids were allowed to settle, and the supernatant was decanted via cannula to a separate flask. An aliquot was titrated with iodine in anhydrous tetrahydrofuran, typically the reagent is measured between 0.55 and 0.65M.

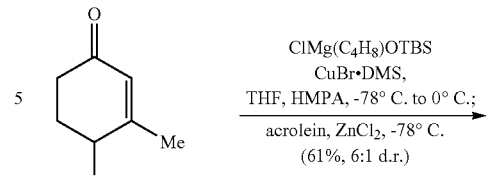

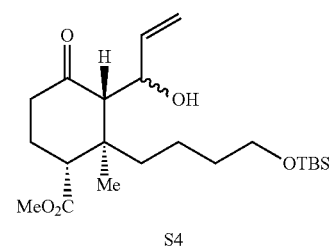

Allylic Alcohol S4.

Copper(I) Bromide-dimethylsulfide complex (29 g, 141 mmol) was suspended in a mixture of anhydrous tetrahydrofuran (250 mL) and anhydrous HMPA (34.4 mL, 198 mmol). The suspension was cooled to −30° C. and stirred with a magnetic stir bar for 20 minutes. A tetrahydrofuran solution of Grignard reagent S3 (460 mL, 0.63M, 290 mmol) was added via addition funnel, dropwise over 2.5 hours, during which time the temperature was maintained between −25 and −15° C. Once addition was complete, the reaction was stirred between −30° C. and −20° C. for 30 minutes, then cooled to −78° C. and stirred for 20 additional minutes. In a separate flask, a solution of Hagemann's ester (23.2 g, 138 mmol) in anhydrous tetrahydrofuran (460 mL) was prepared and transferred to a second addition funnel. This solution was added dropwise at −78° C. over 1.5 hours, and the glassware was rinsed with anhydrous tetrahydrofuran (30 mL). The reaction was allowed to warm to 0° C. (this took 4 hours on this scale, but less time on smaller batches). TLC samples at 0° C. generally indicated near-complete consumption of Hagemann's Ester S1. The reaction mixture was cooled back to −78° C. and stirred for 15 minutes, during which time another oven-dried addition funnel was installed and charged with a solution of anhydrous zinc chloride (40.8 g, 299 mmol) in anhydrous tetrahydrofuran (450 mL+50 mL). This solution was added at −78° C. over 30 minutes, and the reaction was stirred at −78° C. for an additional 10 minutes. Acrolein (44 mL, 657 mmol) was added over 5 minutes and the reaction was stirred for 5 additional minutes at −78° C. The reaction mixture was quenched with saturated aqueous ammonium chloride (2.5 L), and the flask was stirred vigorously while warming to room temperature. Once at room temperature, 1.2 L ethyl acetate was added, followed by an aqueous solution of Na₂EDTA (110 g in 1.6 L of water), these layers were shaken together (Note 1). The aqueous layer was separated, while the organic layer and aqueous/organic emulsion were filtered through Celite and a medium frit; this filter was washed with water and ethyl acetate. The (newly separable) layers were separated, the aqueous fractions were combined and extracted with ethyl acetate (3×500 mL). The combined organic fractions were washed with water (2×500 mL) and brine (500 mL). The organic layer was dried with magnesium sulfate, filtered, and stored at 4° C. overnight. The solvent was removed in vacuo (Note 2). The crude mixture was purified by flash column chromatography with 1.2 kg of silica in a 13 cm diameter column, with a gradient of 10% EtOAc/Hexanes→15%→20%→25% EtOAc/Hexanes. The combined fractions (Note 3) were concentrated in vacuo to give a yellow oil which weighed 35 g (84.8 mmol, 61.4%).

Note 1. On this scale, an intractable blue-green precipitate complicated workup and rendered separation of the aqueous and organic layers impossible. Any filtration fine enough to sufficiently to remove the precipitate completely clogged the filter. Adding disodium EDTA solubilized enough of the unidentified precipitate to make the mixture workable, but some precipitate (and therefore emulsion) remained.

Note 2. The crude mixture was extremely prone to bumping.

Note 3. The fractions that were collected were typically contaminated with unidentified acrolein dimers/polymers; these impurities did not hamper the following reaction.

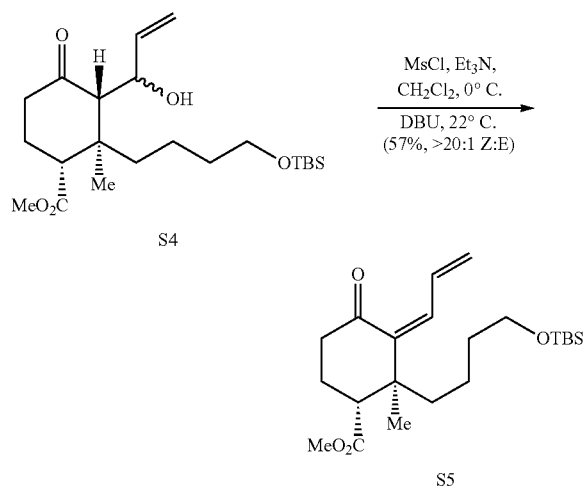

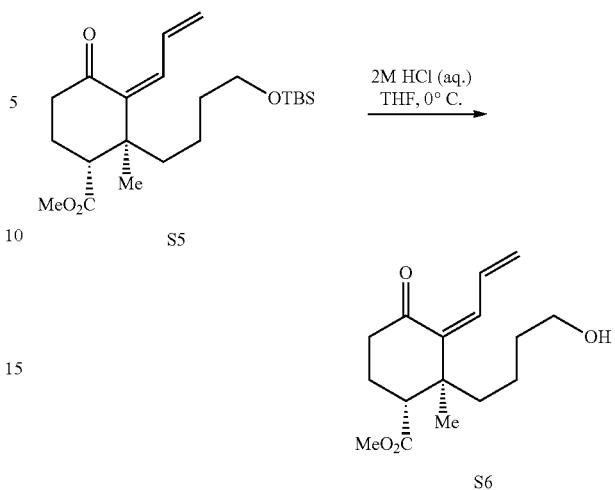

Alcohol S6.

Enone S5 (18.9 g, 47.9 mmol) was dissolved in tetrahydrofuran (750 mL) and stirred with a magnetic stir bar at 0° C. for 20 minutes. Aqueous 2N hydrochloric acid (120 mL) was added over ten minutes, and the reaction was stirred at 0° C. until it was determined by TLC that the starting material was consumed, typically 2 hours. The reaction mixture was quenched with saturated aqueous sodium bicarbonate (500 mL) and the homogeneous mixture was stirred until it reached 22° C. Ethyl acetate (150 mL) was added, resulting in the aqueous and organic layers separating immediately. The resulting biphasic mixture was stirred vigorously for 20 minutes, and the layers were separated. The aqueous layer extracted with ethyl acetate (2×200 mL) and the organic fractions were combined. The organic layer was washed with water (250 mL), washed with brine (250 mL), dried with magnesium sulfate, filtered, and concentrated in vacuo. The impurities did not interfere with the subsequent reaction and the crude material was used directly.

Enone S5.

Allylic alcohol S4 (35 g, 84.8 mmol) was dissolved in anhydrous dichloromethane (600 mL) and stirred with a magnetic stir bar at 0° C. Anhydrous triethylamine (30 mL, 215 mmol) was added, followed by the dropwise addition of anhydrous methanesulfonyl chloride (8.5 mL, 109.8 mmol). The reaction was stirred at 0° C. until TLC indicated the allylic alcohol was consumed, typically 2.5 hours. Anhydrous DBU (38 mL, 254 mmol) was added, and the reaction was stirred at 0° C. for an additional 30 minutes. The reaction was warmed to 22° C. and stirred at this temperature for 12 hours. The reaction mixture was quenched with saturated aqueous sodium bicarbonate (300 mL), and the resulting biphasic mixture was stirred vigorously for 30 minutes. The layers were separated, and the aqueous layer was extracted with dichloromethane (3×150 mL). The organic fractions were combined and washed with saturated aqueous ammonium chloride (400 mL), this aqueous layer was re-extracted with dichloromethane (3×100 mL). The organic fractions were combined again and washed with brine (400 mL). The organic layer was dried with magnesium sulfate, filtered, and concentrated in vacuo. The crude mixture was purified by flash column chromatography with 1.2 kg of silica in a 13 cm diameter column, with a gradient of 5% Et₂O/Hexanes→10%→12.5%→15%→20% Et₂O/Hexanes. The combined fractions were concentrated in vacuo, and weighed to 18.9 g (47.9 mmol, 56.5%).

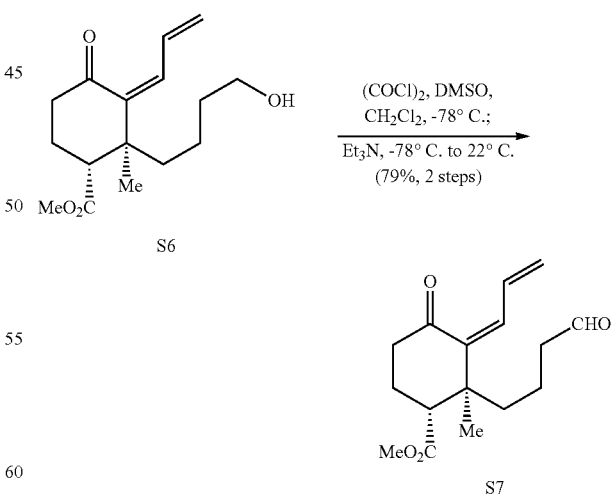

Aldehyde S7.

Oxalyl chloride (10 mL, 115 mmol) was dissolved in anhydrous dichloromethane (300 mL) and stirred with a magnetic stir bar at −78° C. for 10 minutes. In a separate flask, a solution of anhydrous dimethylsulfoxide (17 mL, 239 mmol) in anhydrous dichloromethane (150 mL) was prepared; this solution was added to the oxalyl chloride solution dropwise over 20 minutes. Periodically, the reaction vessel was vented to release built up carbon monoxide pressure. The solution was stirred at −78° C. for 20 minutes. In a separate flask, crude alcohol S6 (<47.9 mmol) was dissolved in anhydrous dichloromethane (300 mL); this solution was added to the reaction mixture dropwise over 20 minutes. The solution was stirred at −78° C. for 30 minutes, at which time anhydrous triethylamine (50 mL, 359 mmol) was added dropwise over 15 minutes. The solution was stirred at −78° C. for 30 minutes, then stirred at 22° C. for one hour. The reaction mixture was quenched with water (700 mL), the layers were separated, and the aqueous layer was extracted with dichloromethane (2×250 mL). The organic fractions were combined, washed with brine (400 mL), dried with magnesium sulfate, filtered, and concentrated in vacuo. The crude mixture was purified by flash column chromatography with 750 g of silica in an 8 cm diameter column, with a gradient of 20% EtOAc/Hexanes→25%→30% EtOAc/Hexanes. The combined fractions were concentrated in vacuo to give a yellow oil which weighed 10.5 g (37.7 mmol, 78.7% over two steps).

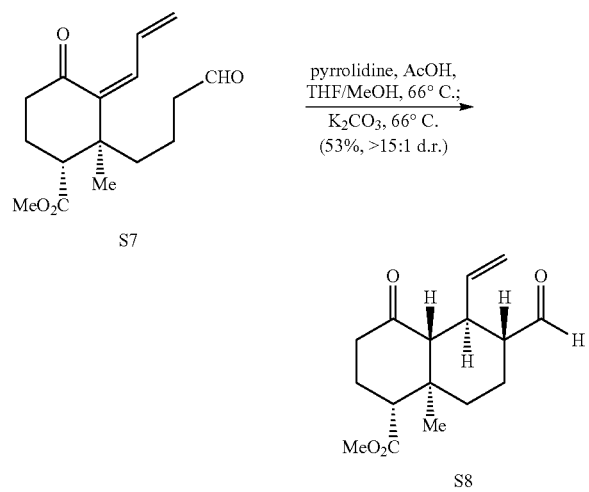

Bicycle S8.

Aldehyde S7 (10.5 g, 37.7 mmol) was dissolved in a mixture of anhydrous tetrahydrofuran (250 mL) and anhydrous methanol (300 mL) and stirred with a magnetic stir bar at 22° C. To this solution was added pyrrolidine (6.2 mL, 75.0 mmol), then glacial acetic acid (4.5 mL, 78.6 mmol). The solution was stirred at reflux until TLC indicated the consumption of the enone, typically 2.5 hours. Anhydrous potassium carbonate (26 g, 188 mmol) was added, and the heterogeneous mixture was stirred vigorously at reflux until TLC indicated the complete equilibration of diastereomers, typically 3 hours. At this point, the reaction was cooled to room temperature, and quenched with aqueous 1N hydrochloric acid (500 mL). Ethyl acetate (500 mL) and additional water (400 mL) were added to induce separation. The layers were separated, and the aqueous layer was extracted with ethyl acetate (3×175 mL). The organic fractions were combined, and washed with saturated aqueous sodium bicarbonate (2×200 mL), then with brine (200 mL). The solution was dried with magnesium sulfate, filtered, and concentrated in vacuo. The crude mixture was purified by flash column chromatography with 600 g of silica in an 8 cm diameter column, with a gradient of 15% EtOAc/Hexanes→20%→25%→30% EtOAc/Hexanes. The combined fractions were concentrated in vacuo to give a yellow solid which weighed 5.5 g (19.8 mmol, 52.5%).

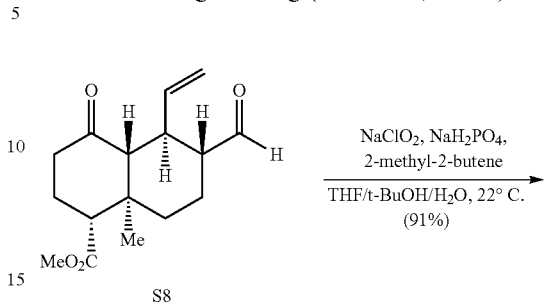

Carboxylic Acid S9.

Bicycle S8 (5.5 g, 19.8 mmol) was dissolved in a mixture of tert-butanol (300 mL) and tetrahydrofuran (300 mL) and stirred with a magnetic stir bar at 22° C. 2-methyl-2-butene (85 mL, 802 mmol) was added, followed by monobasic sodium phosphate (9.5 g, 79.2 mmol) as a solution in water (75 mL). Solid sodium chlorite (6.2 g, 68.6 mmol) was added to the mixture in one portion; the reaction was then stirred at 22° C. until TLC indicated consumption of the aldehyde, typically 2.5 hours. The reaction mixture was quenched with water (500 mL) and diluted with ethyl acetate (500 mL). The layers were separated (Note 4) and the aqueous layer was extracted with ethyl acetate (3×150 mL). The organic fractions were combined, washed with brine (200 mL), dried with magnesium sulfate, filtered, and concentrated in vacuo. The crude solid was purified by azeotropic removal of contaminants with toluene to give a faintly yellow solid which weighed 5.3 g (18.0 mmol, 91.1%).

Note 4:

Further acidification of the aqueous layer beyond what the sodium phosphate naturally effects resulted in marginally improved mass recovery, but an unidentified oxidant was carried into the organic phase. This contaminant interfered with future reactions.

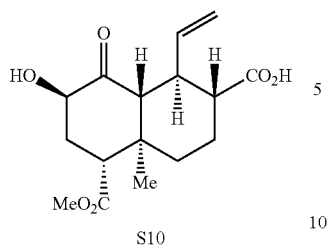

S10

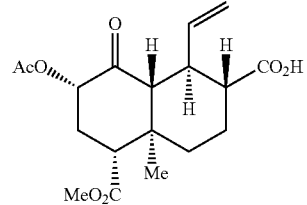

S11

Alcohol S10.

Anhydrous diisopropylamine (1.5 mL, 10.7 mmol) was dissolved in anhydrous tetrahydrofuran (24 mL), cooled to −78° C., and stirred with a magnetic stir bar. Freshly titrated n-butyllithium as a solution in hexanes (4.65 mL, 2.31 M, 10.7 mmol) was added dropwise over 5 minutes. The solution was stirred at −78° C. for 5 minutes, then 0° C. for 10 minutes, then −78° C. for 10 minutes. In a separate flask, a solution of carboxylic acid S9 (1.5 g, 5.10 mmol) in anhydrous tetrahydrofuran (50 mL) was prepared, then added dropwise to the LDA solution over 10 minutes via cannula. The transfer flask was rinsed with additional anhydrous tetrahydrofuran (10 mL) and added via the same cannula. The reaction was stirred at −78° C. for 1 hour. In a separate flask, Davis oxaziridine (1.56 g, 5.97 mmol) was dissolved in anhydrous tetrahydrofuran (25 mL), then added dropwise over 5 minutes via cannula. The transfer flask was rinsed with additional anhydrous tetrahydrofuran (10 mL) and added via the same cannula. The reaction was stirred at −78° C. for 30 minutes, then warmed to 0° C. for 30 minutes. The reaction was quenched with aqueous 1N hydrochloric acid (75 mL) and diluted with ethyl acetate (75 mL). The layers were separated, the aqueous layer was verified to be pH 2 or lower, and the aqueous layer was then extracted with ethyl acetate (2×50 mL). The organic fractions were combined, washed with a mixture of aqueous 1N hydrochloric acid (50 mL) and brine (50 mL), dried with magnesium sulfate, filtered, and concentrated in vacuo. The crude mixture was purified by flash column chromatography in a 5.5 cm diameter column, with a gradient of 3% AcOH/5% Et$_2$O/DCM→3% AcOH/10% Et$_2$O/DCM→5% AcOH/15% Et$_2$O/DCM (Caution: these solvent mixtures cause an exotherm when added to silica and rapidly degrade nitrile gloves). The combined fractions were concentrated in vacuo to give a colorless solid which weighed 950 mg (3.06 mmol, 60.0%).

Acetate S11.

Alcohol S10 (791 mg, 2.55 mmol) was dissolved in anhydrous acetonitrile (50 mL). To this solution was added anhydrous DBU (2.0 mL, 13.4 mmol), followed by solid 4-(dimethylamino)pyridine (38 mg, 0.31 mmol). Acetic anhydride (0.49 mL, 5.19 mmol) was added at 22° C., and the solution was stirred at this temperature until LCMS indicated complete conversion to the acetate, typically 2 hours (Note 5). After acetylation was deemed complete, the flask was fitted with an oven-dried reflux condenser and heated to reflux. The epimerization was monitored by NMR (A variety of LCMS and TLC conditions were unable to separate the diastereomers). When an NMR of an aliquot indicated 4.5:1 dr, the flask was cooled to 22° C. and saturated aqueous sodium bicarbonate (50 mL) was added. The mixture was stirred at 22° C. for 1 hour. The mixture was diluted with ethyl acetate (50 mL) and acidified with aqueous 1N hydrochloric acid (75 mL). The layers were separated, the aqueous layer was verified to be pH 2 or lower, and the aqueous layer was then extracted with ethyl acetate (2×50 mL). The organic fractions were combined, washed with a mixture of aqueous 1N hydrochloric acid (25 mL) and brine (25 mL), dried with magnesium sulfate, filtered, and concentrated in vacuo. The crude mixture was purified by flash column chromatography in a 5.5 cm diameter column, with a gradient of 3% AcOH/30% EtOAc/Hexanes→3% AcOH/40% EtOAc/Hexanes→5% AcOH/45% EtOAc/Hexanes. The combined fractions were concentrated in vacuo to give a yellow solid which weighed 755 mg (2.14 mmol, 83.9%).

Note 5:

LCMS samples indicate the starting material is consumed rapidly, forming the acid anhydride. The mass of the product of the first half of this step corresponds to the mass of the starting material+2 acetyl groups

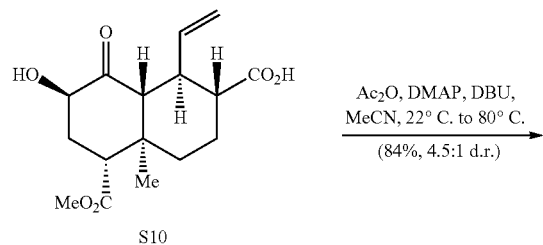

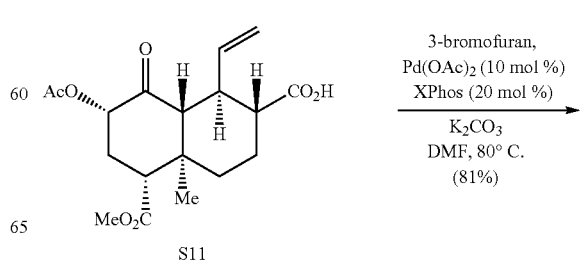

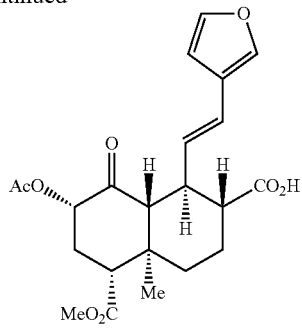

S12

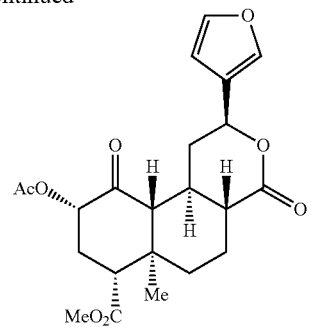

nor-20-salvinorin A

Furan S12.

A solution of acetate S11 (357 mg, 1.01 mmol) in anhydrous DMF (13 mL) was degassed by bubbling with Argon while sonicating for 10 minutes. 2-Dicyclohexylphosphino-2',4',6'-triisopropylbiphenyl, or 'XPhos' (100 mg, 0.21 mmol) was added, followed by anhydrous potassium carbonate (554 mg, 4.01 mmol). Palladium(II) acetate (25 mg, 0.11 mmol) was added and the solution was stirred at 22° C. for 10 minutes. 3-bromofuran (0.22 mL, 2.45 mmol) was added, and the solution was heated to 80° C. (Note 6) and stirred with a magnetic stir bar until LCMS indicated consumption of the starting material, typically 2.5 hours. When the reaction was deemed complete, the reaction was cooled to 22° C., quenched with aqueous 1N hydrochloric acid (25 mL) and diluted with ethyl acetate (20 mL). The layers were separated, the aqueous layer was verified to be pH 2 or lower, and the aqueous layer was then extracted with ethyl acetate (2×25 mL). The organic fractions were combined, washed with aqueous 1N hydrochloric acid (4×15 mL), then washed with a mixture of aqueous 1N hydrochloric acid (15 mL) and brine (15 mL). It was then dried with magnesium sulfate, filtered, and concentrated in vacuo. The crude mixture was purified by flash column chromatography in a 4.5 cm diameter column, with a gradient of 3% AcOH/25% Acetone/Hexanes→3% AcOH/30% Acetone/Hexanes→5% AcOH/35% Acetone/Hexanes. The combined fractions were concentrated in vacuo to give a yellow solid which weighed 344 mg (0.822 mmol, 81.4%).

Note 6.

Preliminary reactions to optimize this process were irreproducible due to hot DMF leeching sulfur-containing contaminants from the rubber septa used to seal the reaction vessels. These contaminants caused catalyst death. A reflux condenser that ensures the DMF vapor doesn't reach the septum is imperative.

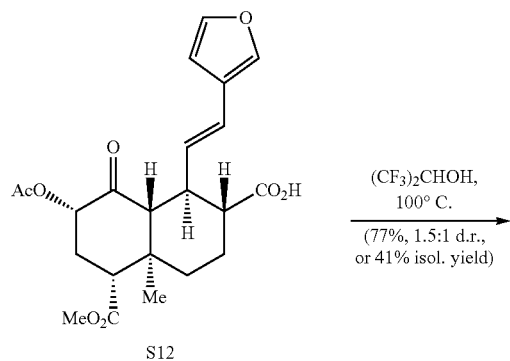

20-Nor-Salvinorin A.

An oven-dried 100 mL pressure tube equipped with a magnetic stir bar was charged with furan S12 (344 mg, 0.822 mmol) as a solution in anhydrous hexafluoroisopropanol (12 mL). The reaction vessel was sealed and heated to 100° C. for 18 hours. An aliquot was taken and analyzed by NMR; it indicated a mixture of 49% 20-nor-salvinorinA, 30% of the C-12 epimer, and 21% of the uncyclized alkene. (Note 7). The reaction was cooled to 22° C., diluted with ethyl acetate (30 mL), and washed with aqueous 1N hydrochloric acid. The layers were separated, and the aqueous layer was extracted with ethyl acetate (2×20 mL). The organic fractions were combined, washed with a mixture of aqueous 1N hydrochloric acid (15 mL) and brine (15 mL), dried with magnesium sulfate, filtered, and concentrated in vacuo. The crude mixture was purified by flash column chromatography in a 4.5 cm diameter column, with a gradient of 35% EtOAc/Hexanes→45% EtOAc/Hexanes. The combined fractions were concentrated in vacuo to give a yellow solid weighing 140 mg (0.335 mmol, 40.7%). The fractions contaminated with the C-12 epimer and unreacted alkene could be concentrated to 200 mg and resubjected to the reaction conditions.

Note 7:

Due to the reversibility of this reaction, allowing it to proceed further would not increase the isolated yield of the desired diastereomer.

Biological Methods and Results

Cell Based Signaling Assays

The competition binding studies were performed on CHO-K1 cells expressing the human KOR (CHO-hKOR). CHO-hKOR membranes were prepared in 50 mM Tris, 100 mM NaCl and 1 mM EDTA by dounce homogenization, followed by centrifugation at 20,000×g for 30 minutes. Membranes (10 µg) were incubated with 1 nM [$^3$H]-U69,593 (PerkinElmer) and increasing concentrations of the test compounds in buffer containing 10 mM Tris and 100 mM NaCl for 2 hours at 25° C. The assay was terminated via filtration through GF/B glass fiber filters pretreated with 0.1% polyethyleneimine on a Brandel cell harvester. Filters were counted with Microscint on a TopCount NXT microplate scintillation counter (PerkinElmer). Nonspecific binding was determined in the presence of 10 µM U69,593. Total receptor number was determined by [$^3$H]-U69,593 saturation binding ($K_D$=1.07 nM, BMax=708 fmol/mg protein). Inhibition of cAMP was determined by incubating CHO-hKOR cells (4,000 cells/well in low-volume 384-well plates) with the test ligands and 25 µM RO-20-1724 (Sigma Aldrich) and 20 µM forskolin (Sigma Aldrich) for 30 minutes at 25° C. The CISBIO cAMP HTRF HiRange assay was used to quantify cAMP levels according to the manufacturer's instructions. The βarrestin2 recruitment assay was performed using the DiscoveRx PathHunter enzyme complementation assay (PathHunter U2OS OPRK1 parrestin cell line) according to the manufacturer's instructions. Cells (5,000 cells/well of a 384-well plate) were incubated with test compounds for 1.5 hours at 37° C. prior to cell lysis.

Chloroquine Phosphate-Induced Pruritus

Experiments were carried out with 10-14 week male C57BL/6J mice purchased from The Jackson Laboratory. Mice were group housed (3-5 mice/cage) and maintained on a 12-hour light/dark cycle. All mice were cared for in accordance to the guidelines set forth by the National Institutes of Health and with the approval of The Scripps Research Institute Animal Care and Use Committee. To determine the ability of the agonists to block chloroquine phosphate (Sigma Aldrich) induced pruritus, mice were habituated to the testing boxes for 1 hour and then pretreated with either vehicle (1:1:8, DMSO: Tween 80: 0.9% sterile saline) or 3 mg/kg U50,488H, nor-20-salvinorin A or salvinorin A (10 μl/g, s.c.-flank) for 10 minutes. Mice were then challenged with 40 mg/kg chloroquine phosphate (5 μl/g, s.c.-neck) and the number of scratching bouts were counted in 5 minute intervals for 1 hour by a blinded investigator.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of formula 20-nor-salvinorinA

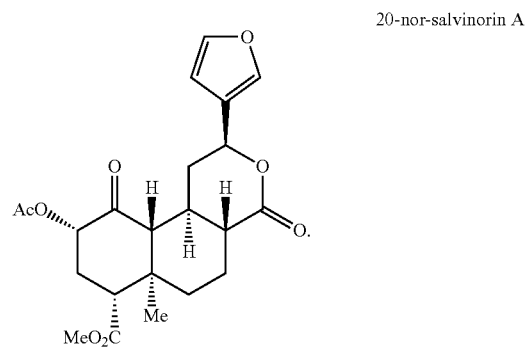

20-nor-salvinorin A

2. A pharmaceutical composition comprising the compound of claim 1 and a pharmaceutically acceptable excipient.

3. A method of modulating a kappa-opioid receptor, comprising contacting the kappa-opioid receptor with an effective amount or concentration of a compound of claim 1.

4. A method of treating a medical condition in a patient, wherein modulation of a kappa-opioid receptor is medically indicated, comprising administering to the patient an effective dose of the compound of claim 1.

5. The method of claim 4, wherein the medical condition is selected from pain, pruritis, depression, or inflammation, or conditions implicating perception and consciousness.

6. A method for treatment of a medical condition in a patient, comprising administering to the patient an effective dose of the compound of claim 1, wherein the medical condition is selected from pain, pruritis, depression, or inflammation, or conditions implicating perception and consciousness.

* * * * *